United States Patent [19]

Mansour et al.

[11] Patent Number: 4,622,298

[45] Date of Patent: Nov. 11, 1986

[54] DETECTION AND QUANTITATION OF MICROORGANISMS, LEUKOCYTES AND SQUAMOUS EPITHELIAL CELLS IN URINE

[75] Inventors: James D. Mansour, Raleigh; Thomas H. Schulte, Cary; Burton H. Sage, Raleigh, all of N.C.

[73] Assignee: Becton, Dickinson and Company, Franklin Lakes, N.J.

[21] Appl. No.: 639,055

[22] Filed: Aug. 9, 1984

[51] Int. Cl.$^4$ .......................... C12Q 1/04; C12Q 1/02; G01N 21/64; G01N 33/48

[52] U.S. Cl. .................... 435/34; 250/461.2; 356/39; 424/3; 435/29

[58] Field of Search ............ 435/34, 29; 356/39; 250/461.2; 424/3

[56] References Cited

U.S. PATENT DOCUMENTS

| | | | |
|---|---|---|---|
| 3,883,247 | 5/1975 | Adams | 356/36 |
| 4,225,783 | 9/1980 | Palin et al. | 435/29 |
| 4,492,752 | 1/1985 | Hoffman et al. | 435/7 |
| 4,500,641 | 2/1985 | Van den Engh et al. | 435/29 |
| 4,508,821 | 4/1985 | Mansour et al. | 250/461.2 |

OTHER PUBLICATIONS

Stamm, U. E., Proceeding of a Symposium on Body Fluids and Infectious Diseases, p. 53, Jul. 28, 1983.
Pollock, H. M., Proceeding of a Symposium on Body Fluids and Infectious Diseases, p. 79, Jul. 29, 1983.
Stamm, U. E., N. Engl. J. Med., 307, 463 (1982).
BAC-T-SCREEN TM System, Marion Scien., Kansas City, MO.
CHEMSTRIP TM, Biodynamics, Indianapolis, IN.

*Primary Examiner*—Sidney Marantz
*Assistant Examiner*—Louanne C. Krawczewicz
*Attorney, Agent, or Firm*—Richard E. Brown

[57] ABSTRACT

A method for the assessment of bacteriuria and pyuria includes the simultaneous detection and quantitation of microorganisms, leukocytes and squamous epithelial cells in a urine specimen. The three cell types are stained with a fluorescent dye, and the urine specimen is analyzed directly, preferably by a single flow microfluorometry protocol.

11 Claims, No Drawings

DETECTION AND QUANTITATION OF MICROORGANISMS, LEUKOCYTES AND SQUAMOUS EPITHELIAL CELLS IN URINE

BACKGROUND OF THE INVENTION

1. Field of the Invention

This invention relates to the analysis of a body fluid, and more particularly relates to a method for the assessment of a bacteriuria by the rapid and simultaneous detection and quantitation of microorganisms, leukocytes and squamous epithelial cells in urine.

2. Description of the Prior Art

Bacteriuria is defined conventionally as the presence of significant numbers of pathogenic microorganisms in the urine, and can arise from colonization of the urine or from urinary tract infection. Colonization in the urinary tract is defined conventionally as replication of organisms normally found in the urine which is not accompanied by invasion of adjacent epithelial and subepithelial tissues. Urinary tract infection is defined conventionally as bacteriuria accompanied by clinical, histologic, or immunologic evidence of host injury.

Urine specimens represent a large portion of the samples received by a clinical diagnostic laboratory. In collection of urine specimens, care must be taken to avoid contamination. Contamination is defined as the inadvertent entry into the collecting vessel of microorganisms normally found in tissues surrounding the urinary tract, and most often is a problem in specimen collection from female patients.

Current methodology used for the detection and quantitation of bacteriuria involves culturing of the microorganisms in the specimen. In these methods, aliquots of urine (usually 1-10 ul) are plated onto various agar type surfaces, cultured for 18-24 hours, and the colonies are counted. In culturing methods, the appearance of colonies of three or more types of organisms suggests specimen contamination.

Screening methods which do not rely on organism growth have been introduced for the rapid detection of bacteriuria. In general, the purpose of screening is to identify and eliminate those urine specimens, generally referred to as negatives, that do not contain significant numbers of microorganisms. Screening, however, is complicated by the fact that urine is not, even in healthy individuals, a sterile fluid, and there has been considerable debate about what urinary microorganism levels indicate infection and what levels are normal. Reviews of this subject in light of conventional methods of urine culture have been presented by Stamm and by Pollock (Am. J. Medicine, Proceedings of a Symposium on Body Fluids and Infectious Diseases, p. 53 and 79, July 28, 1983). Most investigators now consider significant bacteriuria to be defined as the presence of pathogenic microorganisms in a urine specimen at levels of $1 \times 10^4$-$1 \times 10^5$ colony forming units (cfu)/ml and greater. Recent studies, however, by Stamm et al., N. Engl. J. Med. 307, 463 (1982), have shown that defining urinary tract infection as $1 \times 10^5$ cfu/ml resulted in a sensitivity of only about 50% for symptomatic patients.

The Gram stained smear of uncentrifuged urine specimens is occasionally used as a conventional screening procedure for bacteriuria with a high accuracy for predicting negatives. However, the method is highly labor intensive and is not deemed practical when large numbers of samples are received daily. Recently, other nongrowth methods have been developed. The BAC-T-SCREEN TM system, Marion Scientific, Kansas City, Mo., is based on filtration and staining and identifies positive urine specimens which warrant further study via plating. The LUMAC TM system, (3M Co., Minneapolis, Minn.) is based on detection of bacterial adenosine triphosphate and identifies positive specimens in 30 minutes.

For those urine specimens for which either a culturing or screening procedure indicates a significant bacteriuria, differentiation between specimen contamination, colonization and infection is generally carried out. If the bacteriuria is accompanied by large numbers of squamous epithelial cells, specimen contamination is indicated as a possible cause of the bacteriuria. In general, a threshold level of $1 \times 10^4$ squamous epithelial cells per ml of urine specimen is considered to be indicative of contamination. In the art, epithelial cell counts are conventionally carried out during urinalysis in a hemocytometer or by staining a smear of a centrifuged urine specimen.

In the absence of specimen contamination, differentiation of colonization and infection is generally done by measuring the level of pyuria (the presence of leukocytes in the urine). Leukocytes are normally present in urine, and careful studies have established the threshold limit for pathological pyuria as about $1 \times 10^4$ leukocytes/ml of uncentrifuged urine. Pyuria correlates closely with acute symptomatic infection, and its presence may warrant further study of urine specimens in which microorganism counts are less than accepted threshold levels.

Several methods have been developed for assessment of pyuria. These include measurement of leukocyte counts obtained in a hemocytometer or in the high power field of a microscope on spun or unspun urine samples. These methods all have high variability and require too much time and effort for routine clinical use. A currently available dip-and-read test strip based on leukocyte esterase (CHEMSTRIP TM, Biodynamics, Indianapolis, IN.) changes color when dipped into urine containing more than $1 \times 10^5$ leukocytes/ml.

All currently available systems for detection of bacteriuria suffer from disadvantages. Growth based methods have the disadvantages of the time required for culturing and the cost of materials and labor used on samples which ultimately prove negative. Methods in which urine specimens are designated as negatives on the basis of microorganism counts alone (Gram stain, LUMAC TM and BAC-T-SCREEN TM) run the risk of missing positive urine specimens from true urinary tract infections in which the microorganism counts are less than the accepted threshold value of significant bacteriuria ($1 \times 10^5$ cfu/ml). The Gram stain, LUMAC TM and BAC-T-SCREEN TM systems, although providing short analysis time, require substantial hands-on time per sample. CHEMSTRIP TM although quick and inexpensive to use, has the disadvantage of missing some positives. Further, none of the prior art methods assay for all three cell types (microorgansims, leukocytes and squamous epithelial cells) which may be involved in bacteriuria. Current methodology requires separate assays, and these are often carried out in different laboratories. In current practice, microorganism determinations are generally handled in a hospital microbiology laboratory while leukocyte and squamous epithelial cell determinations are handled in the hospital urinalysis laboratory. Thus, there is a need for a better method for the rapid detection of bacteriuria and differentiation of the three cell types often associated with bacteriuria.

SUMMARY OF THE INVENTION

The present invention is a method for assessment of bacteriuria and pyuria. A urine specimen is stained with a fluorescent dye and analyzed by the simultaneous detection and quantitation of microorganisms, leukocytes and squamous epithelial cells.

In a preferred embodiment of the invention, the microorganisms, leukocytes and squamous epithelial cells are stained with the fluorescent dye in the presence of a staining buffer, and the stained specimen is analyzed by a single flow microfluorometry protocol. In a particularly preferred embodiment of the invention, the fluorescent dye is ethidium bromide and the analysis procedure includes the logarithmic scale measurement of multiple flow microfluorometry parameters.

The method of the present invention provides significant advantages over prior art methods for assessment of bacteriuria. A single protocol carried out at a single location identifies and quantitates a bacteriuria and differentiates between microorganisms, leukocytes and squamous epithelial cells in the specimen, thereby determining whether the detected bacteriuria is due to specimen contamination, colonization, or true urinary tract infection. In contrast to conventional culturing methods, the method of the present invention is non-growth dependent and provides results in 20 minutes or less. The method is operationally facile because measurement of the flow microfluorometry parameters by use of the logarithmic scale provides versatility allowing one instrument setting to be used to analyze samples having signals which extend over a very broad range. The method of the invention has the potential to be implemented in clinical diagnostic laboratories and may dramatically reduce the number of urine specimens requiring complete conventional workup, thus resulting in substantially reduced labor and supply costs.

DETAILED DESCRIPTION OF THE INVENTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated. The scope of the invention will be measured by the appended claims and their equivalents.

The present invention is a method for assessment of bacteriuria and pyuria by implementation of a single protocol for the rapid and simultaneous detection/quantitation of microorganisms, leukocytes and squamous epithelial cells in urine. Most microorganisms can be detected by the method of the present invention, such as *Proteus mirabilis, Staphylococcus saprophyticus, Streptococcus fecalis, Lactobacillus casei, Klebsiella pneumoniae, Escherichia coli,* and *Pseudomonus aeruginosa.*

Although it is understood that the invention may be practiced on a clinical urine specimen, the invention is conveniently demonstrated by detection of microorganisms, leukocytes and squamous epithelial cells which have been added to a sterile filtered urine specimen. The microorganisms to be added may be grown in any suitable medium as, for example, Trypticase Soy Broth TM, BBL Microbiology Systems, Cockeysville, Md., removed during the log growth phase, washed with normal saline (0.85% w/v sodium chloride), and suspended in normal saline. The leukocytes to be added may be obtained from any suitable source, as for example, whole blood or whole blood pre-treated with an anticoagulant. Any conventional technique, as for example, dextran sedimentation, may be used to isolate the leukocytes. After isolation, the leukocytes are counted and suspended in normal saline. The squamous epithelial cells to be added to the sterile filtered urine may be obtained from any convenient source, preferably from a culture collection organization such as the American Type Culture Collection, Rockville, Md., and are suspended in normal saline. The concentration of the suspension of microorganisms, leukocytes, and squamous epithelial cells in normal saline thus prepared may be from about $1 \times 10^4$ to $1 \times 10^{10}$, preferably from about $1 \times 10^5$ to $1 \times 10^8$ cfu/ml.

The cell suspensions prepared as above are mixed thoroughly with sterile urine. A urine volume of from about 0.2 to 2.0 ml, preferably from about 0.4 to 1.2 ml is conveniently used. The final concentration of the microorganisms, leukocytes and squamous epithelial cells in the urine may be from about $1 \times 10^3$ to $1 \times 10^8$ preferably from about $1 \times 10^4$ to $1 \times 10^6$ cells of each type per ml.

The urine sample containing microorgansims, leukocytes and squamous epithelial cells is treated with a staining composition. The staining composition contains one or more fluorescent dyes and may contain a staining buffer to enhance absorption of the dye by the cells. Many fluorescent dyes can be used, as for example, thioflavin T, DAPI, 4',6-diamidino-2-phenylindole dihydrochloride 3,3'-dipentyloxacarbocyanine iodide and, preferably ethidium bromide. A variety of buffers is known which enhance dye absorption by cells. Exemplary of such buffers is an aqueous composition containing sodium borate, ethylenediamine tetraacetic acid (EDTA), formaldehyde and a surface active agent. Any surface active agent, such as Triton X-100 TM (trademark of Rohm and Haas Co. for octyl phenoxy polyethoxyethanol), may be used. These reagents may be present in this buffer in concentrations of 40–200 mM, 24–100 mM, 0.02 to 0.1% and 0.02 to 0.1% by volume.

The staining composition may be prepared by adding the fluorescent dye to the staining buffer. The dye is conveniently added as a solution of from about 0.0001% to about 0.01%, preferably from about 0.0005 to 0.005% by weight. Sufficient dye is added to provide a final dye concentration in the staining composition of from about 1 to 100, preferably about 2 to 4 ug/ml by weight. The pH of the staining composition may be adjusted with an alkali metal hydroxide to 7–10, preferably 8.5 to 9.2.

About 1 to 10, preferably about 4, volume parts of the staining composition are added to about 0.2 to 2.0, preferably about 1, volume part of the urine sample containing microorganisms, leukocytes and squamous epithelial cells, and staining is performed by allowing the mixture to stand for from about 1 to 100, preferably about 5 to 20 minutes.

The stained sample may be analyzed by detection of fluorescence emission. A suitable aliquot of the sample is withdrawn and spread over a microscope slide and observed for about 1 minute to 1 hour. The wavelength of the incident light used for excitation depends on the dye used. For example, the incident light when ethidium bromide is used is preferably about 488 nm, and for thioflavin T is preferably about 457 nm. Fluorescence emission may be detected at a wavelength above 520 nm, preferably from about 525 to 700 nm.

Analysis may also be carried out by spectrofluorometry or, preferably, by flow microfluorometry techniques. These procedures are particularly advantageous for detection and quantitation when the microorgansims are present at low levels. In flow microfluorometry techniques, cells which are either naturally fluorescent or labeled with a fluorochrome, are passed, one at a time, through the focused beam from a light source, such as a laser or an arc lamp, whereby they are caused to emit fluorescent signals which are detected. A flow microfluorometry instrument such as a FACS Analyzer or a FACS IV (FACS Division of Becton Dickinson and Company, Sunnyvale, Calif.) may be used. The sample is preferably passed through the beam at a rate of from about 0.05 ml/min to about 0.3 ml/min., preferably about 0.1 ml/min.

In accordance with the preferred method of analysis of the invention using a flow microfluorometer, data may be obtained using multiple parameters of analysis, as, for example, forward and 90° light scatter and red and green fluorescence emission. The data may be presented and stuided using a linear scale or, preferably, a logarithmic scale, or, if desired, some parameters may be studied using a linear scale while others are studied using a log scale. Detection and quantitation of microorganisms, leukocytes and squamous epithelial cells may thereby be carried out simultaneously without changing instrument settings. The determination of suitable parameters of analysis and instrument settings are well known to those skilled in the art and no further details in these respects are needed for a complete understanding of the invention.

The following examples are provided to further illustrate the invention but are not to be construed in any way as limitative of the invention.

EXAMPLE 1

*Proteus mirabilis, Staph. saprophyticus, Strep. faecalis, E. coli,* and *K. pneumoniae* were grown in Trypticase Soy Broth ™ to mid-log phase. The cells were isolated, washed and suspended separately in normal saline to a final concentration of about $1 \times 10^8$ cfu/ml. A 6 ul volume of each organism was added to 0.6 ml of sterile filtered urine in separate tubes and a 0.5 ml aliquot of each was transferred to a second tube. Two ml of a staining buffer/ethidium bromide mixture* was then added to each tube and all tubes were incubated at room temperature for 15 minutes. Inoculum counts were determined by pour plates, and organism counts were determined by a FACS IV flow cytometer. Microorganism recoveries are given below:

| Organism | Inoculum cfu/ml | FACS IV Events/ml | % Recovery |
| --- | --- | --- | --- |
| P. mirabilis | $1.07 \times 10^6$ | $1.03 \times 10^6$ | 93% |
| Staph. saprophyticus | $7.5 \times 10^5$ | $5.48 \times 10^5$ | 73% |
| Strep. faecalis | $1.78 \times 10^6$ | $1.66 \times 10^6$ | 93% |
| E. coli | $1.15 \times 10^6$ | $1.19 \times 10^6$ | 104% |
| K. pneumoniae | $1.40 \times 10^6$ | $1.35 \times 10^6$ | 96% |

*sodium borate, sodium EDTA, formaldehyde and Triton X-100 at concentrations of 100 mM, 60 mM, 0.05% and 0.05% by volume respectively, and 3.125 ug/ml of ethidium bromide, final pH adjusted to 9.2 with sodium hydroxide.

EXAMPLE 2

Four clinical urine specimens (0.5 ml of each) were added to separate tubes and stained in accordance with the procedure of Example 1 using 2.0 ml of the staining buffer-ethidium mixture for each tube. The stained samples were analyzed by a FACS IV flow cytometer for leukocyte detection and quantitation. The leukocyte recoveries by the flow cytometer were compared with leukocyte counts for the four samples obtained using a hemocytometer counting chamber and are given below:

| Specimen | Hemocytometer Count Leukocytes/ml | FACS IV Events/ml | % Recovery |
| --- | --- | --- | --- |
| 1 | $1.4 \times 10^5$ | $1.2 \times 10^5$ | 86 |
| 2 | $1.4 \times 10^5$ | $1.3 \times 10^5$ | 93 |
| 3 | $4.8 \times 10^5$ | $2.3 \times 10^5$ | 48 |
| 4 | $1.4 \times 10^5$ | $1.1 \times 10^5$ | 79 |

EXAMPLE 3

Six clinical urine specimens (0.5 ml of each) in separate tubes were treated with 2.0 ml each of the staining buffer/ethidium bromide mixture of Example 1, and the tubes were allowed to stand at room temperature for 15 minutes. Squamous epithelial cell counts were determined on the FACS IV flow cytometer, and comparative hemocytometer counts were obtained for each of the urine specimens. The results are given below:

| Sample | Hemocytometer Counts (Epithelial Cells/ml) | FACS IV Events/ml |
| --- | --- | --- |
| 1 | $1.7 \times 10^4$ | $1.8 \times 10^4$ |
| 2 | $2.4 \times 10^4$ | $5.0 \times 10^4$ |
| 3 | $8 \times 10^3$ | $1.6 \times 10^4$ |
| 4 | $1 \times 10^4$ | $1.7 \times 10^4$ |
| 5 | $1.1 \times 10^4$ | $2.3 \times 10^4$ |
| 6 | $1.6 \times 10^4$ | $1.5 \times 10^4$ |

EXAMPLE 4

Eight clinical urine samples were subjected to a staining protocol and flow cytometer analysis in accordance with the procedure of Example 2. Analysis of the samples with the FACS IV flow cytometer gave the following cell counts per ml of urine of bacteria, leukocytes and squamous epithelial cells:

| Sample | Bacteria | Leukocytes | Sq. Epith. Cells |
| --- | --- | --- | --- |
| 1 | $2.4 \times 10^4$ | $4.6 \times 10^5$ | $7.3 \times 10^4$ |
| 2 | $1.3 \times 10^6$ | $8.2 \times 10^5$ | $1.5 \times 10^5$ |
| 3 | $3.1 \times 10^4$ | $3.9 \times 10^3$ | $1.4 \times 10^3$ |
| 4 | $5.7 \times 10^3$ | 250 | 536 |
| 5 | $7.0 \times 10^4$ | $2.2 \times 10^3$ | $1.9 \times 10^3$ |
| 6 | $5.5 \times 10^5$ | $7.9 \times 10^3$ | $9.3 \times 10^3$ |
| 7 | $6.1 \times 10^3$ | 120 | 192 |
| 8 | $1.1 \times 10^3$ | 716 | 273 |

The data demonstrate that detection and quantitative cell counts can be determined for all 3 cell types from a single sample processing step.

Thus, in the method of the present invention, a urine specimen is analyzed for microorganisms, leukocytes, and squamous epithelial cells to assess the cause and extent of a bacteriuria. The method includes staining of the three cell types with a fluorescent dye and direct analysis of the urine specimen, preferably by flow cytometry. The three cell types are detected and quantitated simultaneously by a single protocol, in contrast to conventional methods wherein the three cell types are analyzed separately, often in different laboratories. Because only a single protocol is used and the method does not rely on microorganism growth, results are obtained much faster than by conventional culturing procedures.

What is claimed is:

1. A method for the assessment of bacteriuria and pyuria comprising contacting a urine specimen with a staining composition including a fluorescent dye and a staining buffer to provide a mixture and simultaneously detecting and quantitating microorganisms, leukocytes and squamous epithelial cells in said mixture by a single flow microfluorometry protocol.

2. The method in accordance with claim 1 wherein said microorganisms are selected from the group of microorganisms consisting of *Proteus mirabilis, Staphylococcus saprophyticus, Streptococcus fecalis, Lactobacillus casei, Escherichia coli, Klebsiella pneumoniae,* and *Pseudomonus aeruginosa.*

3. The method in accordance with claim 1 wherein said fluorescent dye is selected from the group of dyes consisting of ethidium bromide, thioflavin T, DAPI and 3,3'-dipentyloxacarbocyanine iodide.

4. The method in accordance with claim 1 wherein said composition includes a plurality of fluorescent dyes.

5. The method in accordance with claim 1 wherein said staining buffer comprises sodium borate, ethylenediamine tetraacetic acid, formaldehyde and a surface active agent.

6. The method in accordance with claim 5 wherein said surface active agent is octyl phenoxy polyethoxyethanol.

7. The method in accordance with claim 1 wherein said flow microfluorometry protocol includes obtaining multiple parameter measurements of the urine specimen.

8. The method in accordance with claim 7 wherein said parameter measurements include at least two of forward light scatter, 90° light scatter, red fluorescence emission and green fluorescence emission.

9. The method in accordance with claim 7 wherein said multiple parameter measurements are taken using a logarithmic scale.

10. The method in accordance with claim 9 wherein a single setting of the flow microfluorometer is used.

11. A method for the assessment of bacteriuria and pyuria by analysis of a urine sample for the presence of microorganisms, leukocytes and squamous epithelial cells comprising contacting a urine sample with a staining composition including ethidium bromide and a staining buffer to provide a mixture, incubating said mixture, and analyzing said mixture by a flow microfluorometry protocol including logarithmic scale measurement of forward and 90° light scattering and red and green fluorescence emission after a single setting of the flow microfluorometer.

* * * * *